United States Patent [19]

Stevens

[11] 4,030,483
[45] June 21, 1977

[54] PULSE RATE MONITORING DEVICE

[76] Inventor: Jack D. Stevens, 1229 S. Barkley, Mesa, Ariz. 85204

[22] Filed: Apr. 26, 1976

[21] Appl. No.: 680,136

[52] U.S. Cl. .................... 128/2.05 T; 128/2.05 P
[51] Int. Cl.² .......................................... A61B 5/02
[58] Field of Search .............. 128/2.05 E, 2.05 P, 128/2.05 R, 2.05 S, 2.05 T, 2.06 R

[56] References Cited

UNITED STATES PATENTS

| 3,107,664 | 10/1963 | Smith | 128/2.05 P |
| 3,704,706 | 12/1972 | Herczfeld et al. | 128/2.05 P |
| 3,717,140 | 2/1973 | Greenwood | 128/2.05 T |
| 3,908,636 | 9/1975 | Page | 128/2.05 P X |

Primary Examiner—William E. Kamm
Attorney, Agent, or Firm—Warren F. B. Lindsley

[57] ABSTRACT

A hand-held device which measures the period of a heartbeat, converts the measured period to beats per minute and displays the result on a digital read-out indicator. In using the device, the subject places his thumb in a depression formed in its case. Located in the depression are a light, a photo-sensor and an activating switch. The sensor responds to light transmitted through the thumb, the transmitted light being pulsed as blood is pumped into the thumb by the action of the heart.

5 Claims, 10 Drawing Figures

PULSE RATE MONITORING DEVICE

BACKGROUND OF THE INVENTION

It has long been recognized that the rate and regularity of the heartbeat reflect the physiological condition of the heart. Studies have indicated that variations in the heart action also give warning in many instances of impending heart trouble.

The electrocardiograph gives a good and accurate tracing of heart action, but its use is restricted to the medical office and to those patients whose history or symptoms indicate that a special heart test should be made.

For greater utility and effectiveness a portable device is needed which can be operated by the subject himself in a wide variety of conditions. Joggers or cardiac sufferers, for instance, need to measure their pulse rates periodically in order not to exceed some maximum rate specified by their physicians. A portable instrument useable during periods of activity could provide a means for the determination of safe limits on exercise or other forms of stress.

Such a device must be accurate and easy to use and it should preferably provide a read-out means which is immediately recognizable. It should not be necessary, for example, to count pulses or make calculations or conversions which require time and concentration and are subject to human error.

In order to sense irregularities in the heartbeat as well as the average rate, the device should be capable of taking measurements over relatively brief periods covering no more than a few beats. Readings should be continually repeated to indicate variations.

DESCRIPTION OF THE PRIOR ART

No prior art device has incorporated all of the desired features in a single unit.

Smith (U.S. Pat. No. 3,107,664) offers a piezo-electric transducer which must be taped to the finger and utilized along with additional instrumentation not disclosed in the patent.

Brayshaw et al. (U.S. Pat. No. 3,633,569) discloses an "arrhythmia counter" which measures intervals between heartbeats and registers the number of deviations from normal occurring over an extended period of time. Use of the unit requires supervision by a physician or medical examiner and requires the fastening of electrodes to the patient's chest.

Peek (U.S. Pat. No. 3,835,837) provides a hand-held device which senses heartbeat by means of light passed through the subject's finger. The light signal is converted to a visual or audio signal which is counted by the subject. The device also incorporates an interval timer (6 seconds) and indicates the end of the timing interval by flashing a light or sounding an audible signal distinguishable from that indicating heartbeat.

Page (U.S. Pat. No. 3,908,636) also utilizes light passing through the subject's finger to sense heartbeat. An audible signal which is produced coincident with each beat is counted by the subject over a fixed period of time.

There is an apparent need for an improved device which incorporates the additional important features not provided by the prior art.

SUMMARY OF THE INVENTION

In accordance with the invention claimed, an improved hand-held pulse monitoring device is provided which may be readily and conveniently utilized by any subject in a variety of conditions and circumstances.

It is, therefore, one object of this invention to provide an improved hand-held pulse monitoring device.

Another object of this invention is to provide such a device which is especially easy to employ and does not require the user to perform calculations or conversions demanding concentration or prolonged attention.

A further object of this invention is to provide in such a device a high degree of accuracy and consistency in performance.

A still further object of this invention is to provide such a device which provides a digital read-out of the pulse rate monitored.

A still further object of this invention is to provide such a device which determines the indicated pulse rate as a function of pulse period averaged over a very few beats, such as four, so that brief variations or irregularities in the pulse will be detected and indicated.

A still further object of this invention is to provide such a device which continually repeats its measurements and thereby indicates variations over a longer period of time.

A still further object of this invention is to provide in its structural design a capability for use under conditions of strenuous exercise without inconvenience in any form that might interfere with the physical activity of the user.

Yet another object of this invention is to provide such a device in an inexpensive form which will make it broadly applicable that it may thereby benefit the health and well-being of a large segment of the population.

Further objects and advantages of the invention will become apparent as the following description proceeds and the features of novelty which characterize this invention will be pointed out with particularity in the claims annexed to and forming a part of this specification.

BRIEF DESCRIPTION OF THE DRAWING

The present invention may be more readily described by reference to the accompanying drawing, in which.

DESCRIPTION OF THE PREFERRED EMBODIMENT

Figure 1:
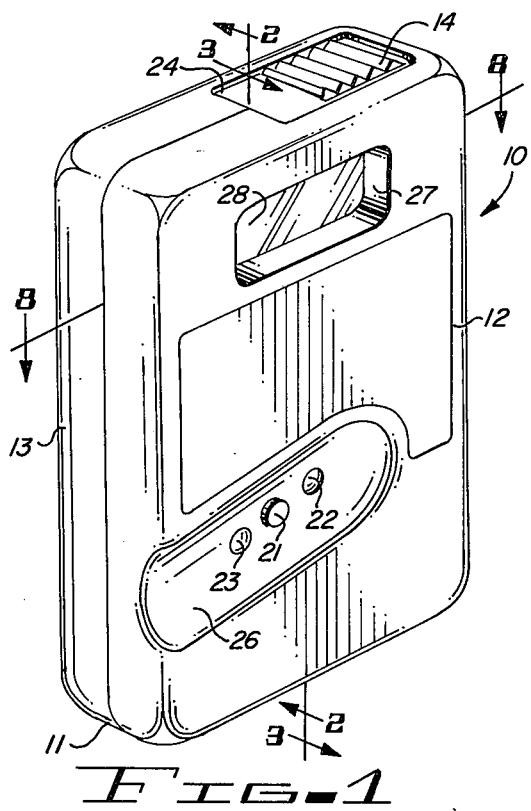
FIG. 1 is a perspective view of the hand-held pulse monitoring device of the invention.
Figure 2:
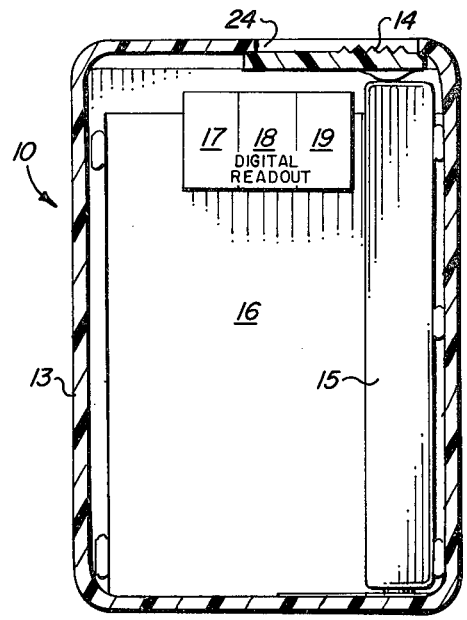
FIG. 2 is a cross-sectional view of the device of FIG. 1 taken along line 2—2 of FIG. 1.

Referring more particularly to the drawing by characters of reference, FIGS. 1–10 discloses an improved pulse monitoring device 10 comprising a three part plastic case 11 including a front member 12, a rear member 13 and a sliding battery cover 14, a storage battery 15, a printed circuit board 16, digital read-out elements 17, 18 and 19, an activating switch 21, a light source 22, and a photo-sensor 23.

Front and rear members 12 and 13 of case 11 take the general form of two rectangular boxes closing on each other to form an enclosure similar in size and shape to a pack of cigarettes. Both parts are molded in plastic and are formed in such a way that they may be snapped together. At the top end of the enclosure so formed there is a rectangular opening 24 positioned at one side over the end of battery 15. Cover 14 is confined with two slots located opposite each other inside the front and rear members 12 and 13 just below the opening 15 so that it may be moved from side to side to clear or block the opening 15. A portion of the top surface of the cover 14 is provided with lateral ridges 25 which project upward to facilitate the opening or closing of the cover 14 by moving it to the right or left, respectively, in FIG. 3.

While rear member 13 of case 11 has a plain rear wall and holds only the printed circuit board 16, front member 12 is specially contoured to meet certain functional requirements of the invention.

Running diagonally across the lower front surface of member 12 is a concave depression 26 contoured to receive the underside of the thumb of the person using the device 10. Positioned along the bottom of this depression are the switch 21, the light source 22 and the photo-sensor 23.

Projecting inward from the outer front surface of member 12 at a central position near the top of member 12 is a rectangular picture frame 27 in which is affixed a transparent plastic or glass window 28. The frame 26 fits around the periphery of the three read-out elements 17, 18 and 19 which are mounted on the printed circuit board 16. Window 27 thus provides visual access to these elements.

Figure 3:
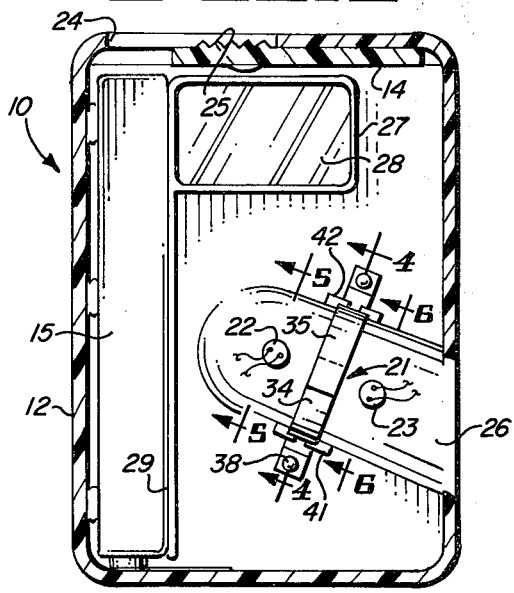
FIG. 3 is a cross-sectional view of the device of FIGS. 1 and 2 taken along line 3—3 of FIG. 1.

A longitudinal projection 29 inside member 12 forms a retaining wall for battery 15. In the view of FIG. 3 the projection 29 is seen to be aligned with the left-hand edge of frame 27 running parallel to the left-hand edge of member 12 but positioned a short distance to the right of it so as to form therebetween a compartment for battery 15. Comparing FIG. 3 with FIG. 1 it is to be noted that this compartment and battery 15 are located along the right-hand edge of case 11 to the right of the depression 26 and directly below opening 24 and cover 14.

Figure 4:
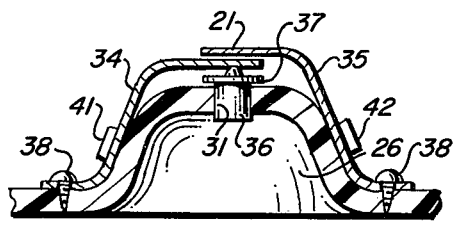
FIG. 4 is a cross-sectional view of the device of FIGS. 1–3 taken along line 4—4 of FIG. 3.
Figure 5:
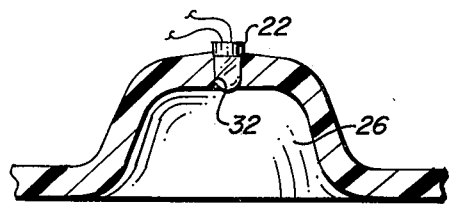
FIG. 5 is a cross-sectional view of the device of FIGS. 1–3 taken along line 5—5 of FIG. 3.
Figure 6:
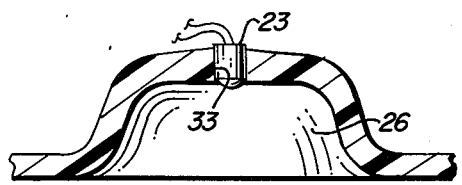
FIG. 6 is a cross-sectional view of the device of FIGS. 1–3 taken along line 6—6 of FIG. 3.
Figure 7:
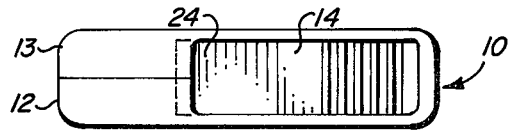
FIG. 7 is a top view of the device of FIGS. 1–3.
Figure 8:
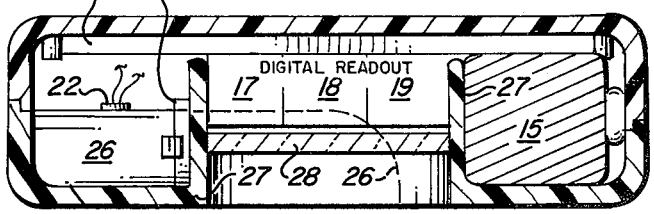
FIG. 8 is a cross-sectional view of the device of FIG. 1 taken along line 8—8 of FIG. 1.

As shown in FIGS. 4, 5 and 6, the switch 21, the light source 22 and the photo-sensor 23 are secured within holes 31, 32 and 33 in the depression 26. The drawings shown switch 21 positioned between source 22 and sensor 23 with sensor 23 located outboard from switch 21. The invention is, of course, not limited to this orientation, and it may be found that the source 22 and the sensor 23 should preferably be located immediately adjacent each other i.e. juxtaposed.

The switch 21 comprises three parts including first and second spring members 34 and 35 and a push button 36. Button 36 projects through hole 31 but is prevented from passing outward through hole 31 by a retaining ring 37 surrounding its tapered inner end. Spring members 34 and 35 are formed from flat strips of phospher-bronze. As shown in FIG. 4 the members 34 and 35 are mounted opposite each other to opposite sides of depression 26, their general alignment running perpendicular to depression 26. Each member has one end secured at the edge of depression 26 by a screw 38. From the screws 38 the contours of members 34 and 35 follow the contour of the depression 26 but continue to a somewhat greater depth before ending toward each other. The free ends of members 34 and 35 in bending toward each other overlap but are not in physical contact in their rest position, member 34 covering the inner tapered end of button 36 so as to trap button 36 inside hole 31. To actuate switch 21, button 36 is depressed by the thumb so that the tapered end of button 36 forces the end of member 34 against the overlapping end of member 35. Electrical contact is thus established between the two screws 38 which serve as electrical terminals for the switch 21. Molded plastic tabs 41 and 42 integral with member 12 grip the edges of members 34 and 35 to further secure their position.

Figure 9:
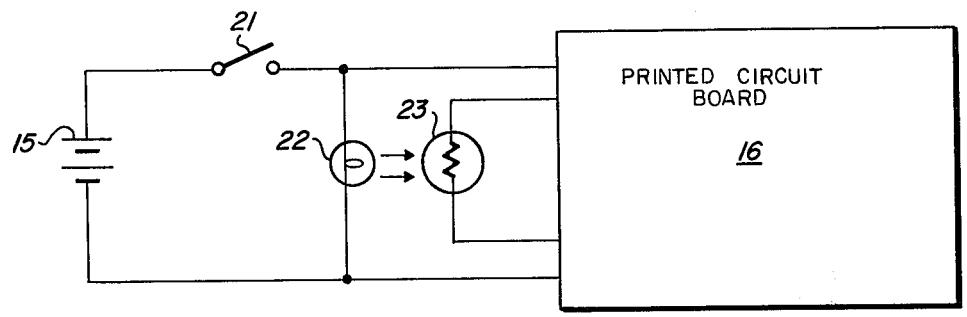
FIG. 9 is an electrical schematic showing interconnections between the elements of the device.

Electrically, the switch 21 is serially connected with the d-c terminals of the printed circuit board 16 across the terminals of the battery 15 as shown in FIG. 9. Light source 22 is connected across the terminals of the printed circuit board and is also across the terminals of the printed circuit board and is also energized when switch 21 is closed. Sensor 23 is also connected to printed circuit board 16.

In the application and operation of the device 10, the user places the thumb of his left hand in the depression 26 covering the switch 21, the light source 22 and the sensor 23. As switch 21 is closed by pressure from the user's thumb, light source 22 is energized and transmits light through the thumb to sensor 23. As blood is pumped into the thumb through the action of the user's heart, the amount of light transmitted through the thumb is modulated thereby so that a pulsating electrical signal coincident with the user's heartbeat is delivered by sensor 23 to printed circuit board 16.

Figure 10:
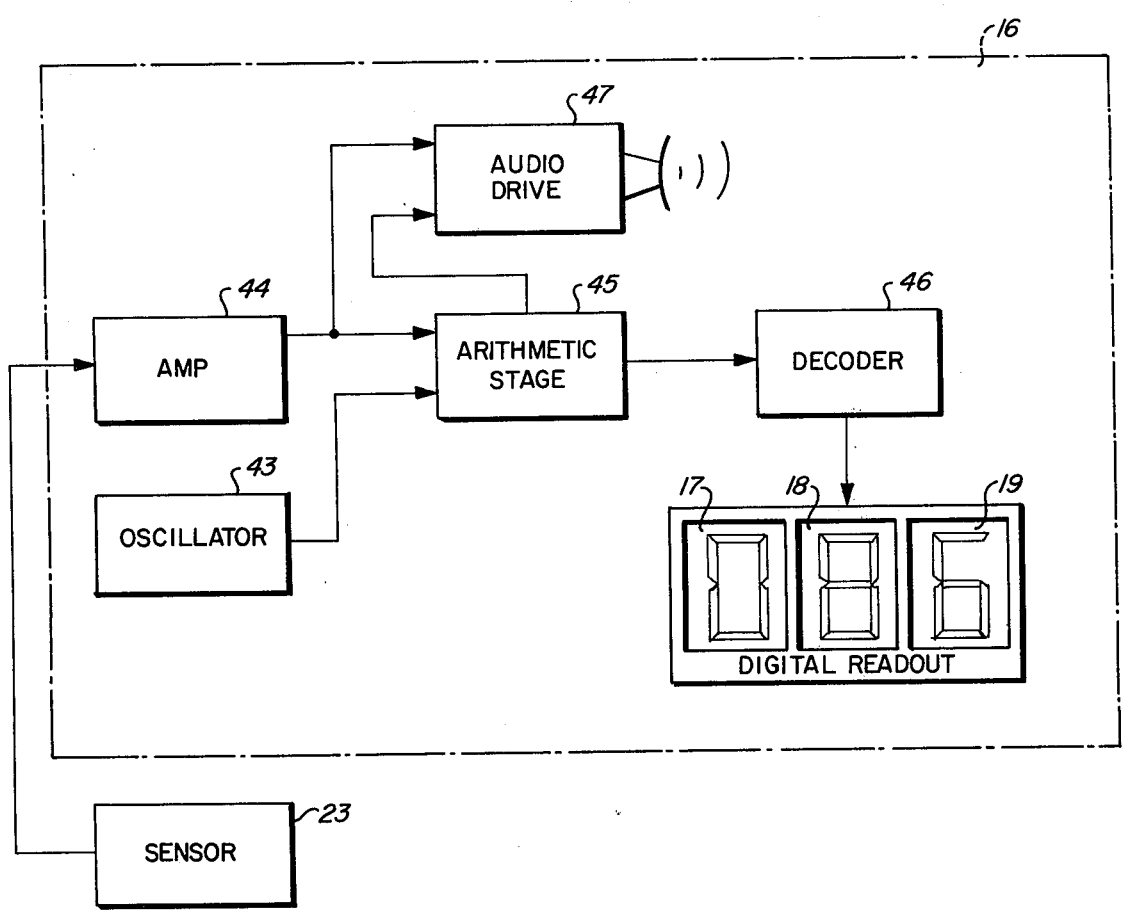
FIG. 10 is a function block diagram of the electronic circuits incorporated in the device.

As shown by FIG. 10, the printed circuit board 16 comprises functionally an osciallator 43, amplifier 44, an arithmetic stage 45, a decoder 46, the digital read-out elements elements 17, 18 and 19 and an optional audio drive stage 47. The sensor 23 is a photo-resistor, its resistive value varying with the intensity of light received from source 22. Sensor 23 is connected to the input terminal of amplifier 44 and delivers to amplifier 44 a voltage pulse coincident with each heartbeat. Amplifier 44 is a low-pass amplifier specifically adapted to pass an electrical pulse corresponding to each individual beat of the heart but to reject other high-frequency noise signals as from other sources such as nearby electrical lighting or noise-generating equipment.

Osciallator 43 is a precision high-frequency osciallator operating at any appropriate fixed frequency as, for example, 67.5 kilohertz. Oscillator 43 serves as a stable time base against which the period of the heartbeat is measured to determine the apparent heart rate.

The output of the amplifier 44 and the output of the oscillator 43 are connected as inputs of the arithmetic stage 45. In the arithmetic stage 45 the period of four heartbeats as indicated by four pulses delivered by amplifier 44 are compared against the time base established by 43 to calculate the apparent heart rate. The binary output of the arithmetic stage 45 is then decoded as required to drive the digital read-out elements 17, 18 and 19.

Each of the elements 17, 18 and 19 is a commercially available seven-segment display element, the seven segments appropriately arranged so that through the selective illumination of the individual segments, any of the 10 digits, zero through nine, may be stimulated. In FIG. 10, for example, the digits "zero", "eight" and "six" are formed suggesting a measured heart rate of 86 beats per minute. Each selected segment is illuminated by energizing a light-emitting diode.

The heartbeat measurement spans the period of four heartbeats as indicated. The calculated heartbeat is set into the digital readout elements 17, 18 and 19 and remains there until the end of the next measurement and calculation, at which time is reading is updated to the new value. Following each calculation, a new reading is present every four heartbeats for as long as the thumb is held in position in the depression 26.

The repeated measurements taken at these relatively short intervals gives the user a running picture of variations in his heartbeat in addition to the indication of the actual rate. Irregularities in the heartbeat are thus made evident.

The optical audio drive stage 47 receives an input from the arithmetic stage 45 in addition to the output signal from amplifier 44. The signal from stage 45 is a subharmonic from oscillator 43 in the audio range. The subharmonic is obtained as an output of a frequency divider driven by oscillator 43. The subharmonic is employed in audio drive stage 47 to modulate the pulse from amplifier 44 at an audio frequency. The modulated pulse is used to drive a transducer to deliver an audible signal coincident with each heartbeat. The audible signal thus provided serves as a further aid in distinguishing irregularities. The audible output may also be employed along with a clock or stop-watch to check the calibration of the device 10 in verification of its proper operation.

For the most part, the circuitry of printed circuit board may be implemented with standard integrated circuits, such as flip-flops, gates, counters, decoders, etc. As demonstrated by current trends in the cost of miniature hand calculators, the cost of implementing similar logic functions is very low even where such functions are considerably more complex than required for this invention.

While the actual implementation of the particular functions shown in FIG. 10 may be accomplished in various ways by those skilled in the art, the general approach as suggested by the functional diagram of FIG. 10 is claimed as part of this invention. This and other features of this invention effectively meet the stated objects of the invention.

Although but a single embodiment of the present invention has been illustrated and described, it will be apparent to those skilled in the art that various changes and modifications may be made therein without departing from the spirit of the invention or from the scope of the appended claims.

What is claimed is:

1. A cardiac monitor comprising:
   a hand-held case comprising two interlocking parts defining an enclosure for housing electronic pulse sensing circuitry,
   one of said parts defining a cover for said case having an exposed indentation in its surface for receiving along at least a part of its length a part of a finger of the hand of the user holding the case,
   electronic circuitry mounted within said case for receiving signals representative of successive pulses of a cardiac wave, counting means for recording said successive pulses sensed, and digital readout means for indicating periodic summations of said counting means, and
   dual purpose means mounted within said indentation and connected to said electronic circuitry for energization of said circuitry and sensing of said successive pulses upon positioning of the finger of the user in said indentation,
   said dual purpose means comprising a switch for electronically energizing said electronic circuitry upon positioning of the finger of a user in said indentation, an electric light bulb energized by said electronic circuitry and illuminating the finger in said indentation, and a sensor connected to said electronic circuitry for sensing the changing illuminated condition of the finger during successive pulses of the cardiac wave,
   said switch electric light bulb and sensor being spacedly arranged within and along the length of said indentation, and
   said indentation comprising an open trough form-fitting the thumb of a user.

2. The cardiac monitor set forth in claim 1 wherein: said electric light bulb and said sensor are adjacent each other in said indentation.

3. The cardiac monitor set forth in claim 2 wherein: said sensor comprises a photo-sensor.

4. The cardiac monitor set forth in claim 1 wherein: said case is provided with a window in the same surface of said case as said indentation for exposing said readout means.

5. The cardiac monitor set forth in claim 1 in further combination with:
   means comprising an audio means for indicating each peak of the cardic wave of the user.

* * * * *